(12) United States Patent
Levin

(10) Patent No.: US 6,618,602 B2
(45) Date of Patent: Sep. 9, 2003

(54) METHOD AND APPARATUS FOR SIMULTANEOUSLY DETERMINING A PATIENT'S IDENTIFICATION AND BLOOD OXYGEN SATURATION

(75) Inventor: Paul D. Levin, Santa Cruz, CA (US)

(73) Assignee: Palco Labs, Inc., Santa Cruz, CA (US)

( * ) Notice: Subject to any disclaimer, the term of this patent is extended or adjusted under 35 U.S.C. 154(b) by 0 days.

(21) Appl. No.: 10/061,131

(22) Filed: Jan. 31, 2002

(65) Prior Publication Data

US 2002/0125991 A1 Sep. 12, 2002

Related U.S. Application Data

(60) Provisional application No. 60/274,431, filed on Mar. 8, 2001.

(51) Int. Cl.[7] .................................................. A61B 5/00
(52) U.S. Cl. ........................................ 600/323; 600/344
(58) Field of Search ................................ 600/310, 322, 600/323, 340, 344; 128/903

(56) References Cited

U.S. PATENT DOCUMENTS 4,857,716 A * 8/1989 Gombrich et al. .......... 128/903
6,364,834 B1 * 4/2002 Reuss et al. ................ 600/300

* cited by examiner

*Primary Examiner*—Eric F. Winakur
(74) *Attorney, Agent, or Firm*—Bruce H. Johnsonbaugh

(57) ABSTRACT

A method and apparatus for simultaneously determining a patient's identification and blood oxygen saturation are provided. An pulse oximeter probe carries a light source such as LEDs or lasers which is used to read patient identification information carried on the patient's wristband by a bar code. Alternately, the patient's wristband incorporates a radio frequency reader chip which contains the patient's identification information and the pulse oximeter probe carries an antenna adjacent its cable so that, when the pulse oximeter is turned on, it reads the chip in the wristband during the same motion with which the patient's oxygen blood saturation is measured with the pulse oximeter.

10 Claims, 2 Drawing Sheets

METHOD AND APPARATUS FOR SIMULTANEOUSLY DETERMINING A PATIENT'S IDENTIFICATION AND BLOOD OXYGEN SATURATION

CROSS-REFERENCE TO RELATED APPLICATION

This application claims the benefit of U.S. Provisional Application Serial No. 60/274,431 filed Mar. 8, 2001 entitled "Method and Apparatus for Identifying a Patient Using a Pulse Oximeter Probe."

BACKGROUND AND SUMMARY OF THE INVENTION

Pulse oximetry is now commonly employed along with non-invasive blood pressure, respiratory rate, and temperature in multi-parameter vital signs monitors. Such monitors are carried by hospital nursing staff from room to room for carrying out routine vital signs checks from four to six times per day. It is common practice for the nursing staff to carry a notebook and record manually various vital signs adjacent to the patient's name.

Since hospital patients invariably wear a wrist bracelet for identification, it would be most convenient to use the wristband to automatically record the patient's name and identification number each time that vital signs are taken. Wristbands with bar codes are not in common use at this time for patient identification, but interest is growing in the use of bar codes for this purpose. Since the pulse oximeter is invariably placed on a patient's finger to obtain oxygen saturation, it would be advantageous to use the same motion to cause the pulse oximeter probe to be used as a bar code reader.

The present invention provides an apparatus and method for simultaneously determining the patient's identification and blood oxygen saturation. The invention utilizes prior art pulse oximeters and prior art bar coded wristbands, for example. These individual prior art items have not heretofore been utilized together to automatically obtain and record the patient's identification together with blood oxygen saturation.

Reading the bar code on the wristband is accomplished by placing a combination emitter/detector in the distal end of the oximeter probe. Since the emitter/detector must pass directly over the bar code, this arrangement requires that the end of the pulse oximeter probe make direct contact with the patient's wristband. No deviation from the wristband is permitted when a simple LED bar coder is employed.

An alternative optical method, using a laser diode or a combination of laser diodes and detectors, enables the user to hold the bar code reader a few inches from the coded strip. The electronics for interpreting the reflected light is somewhat more complicated than with the simpler LED system, and the cost of the laser diodes and the complexity of the electronics makes this alternative method somewhat more costly to manufacture than simply employing an LED and a photodetector at the end of the pulse oximeter probe.

DETAILED DESCRIPTION OF THE DRAWINGS

Figure 1:
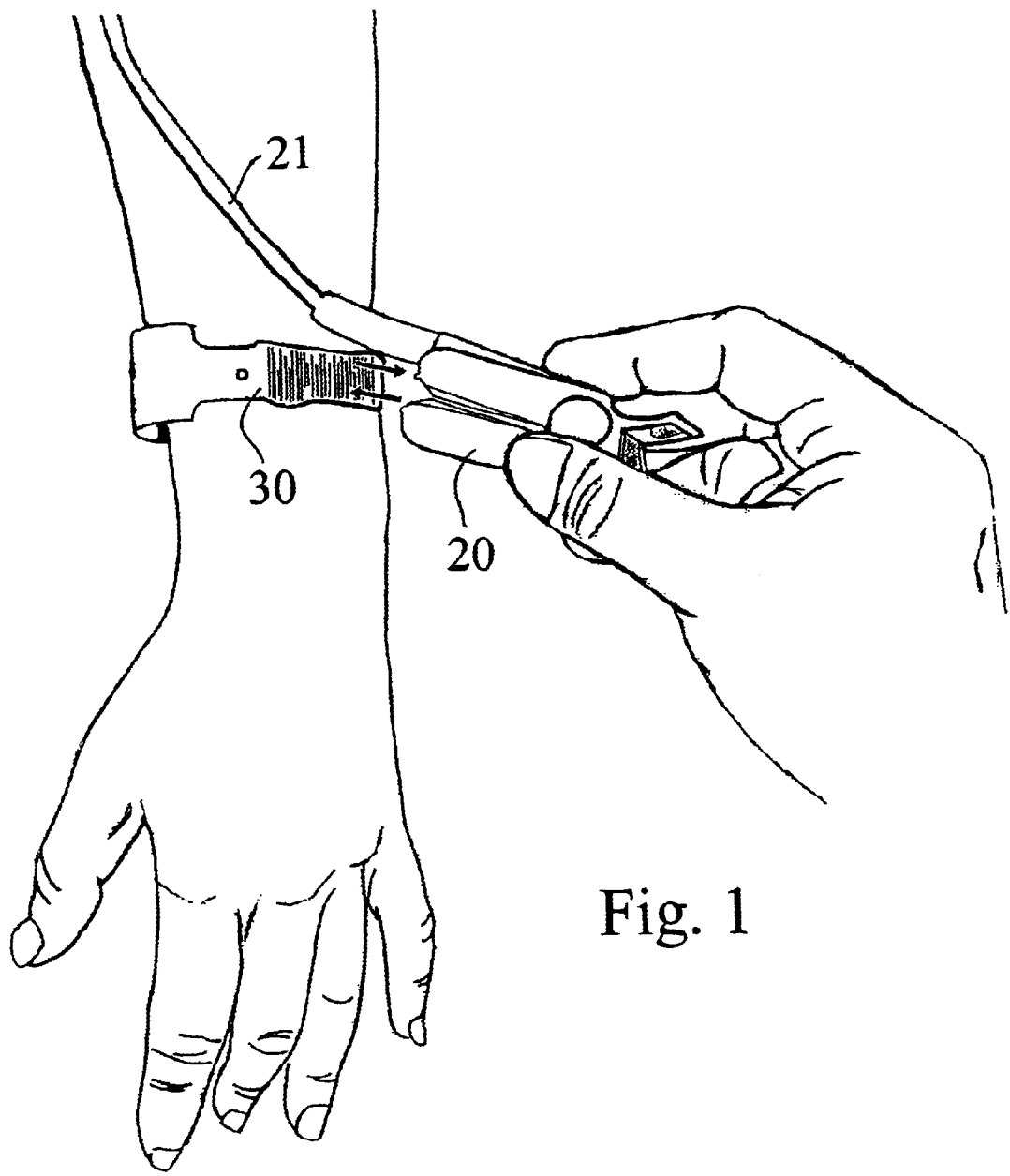
FIG. 1 is a perspective view showing a pulse oximeter probe carrying a fiber optic as it is used to read a bar code on a patient's wristband.

FIG. 1 illustrates a pulse oximeter probe 20 carrying a fiber optic, or LED's and a photodetector, so that a light beam can project to a bar coded wristband 30 and reflect back to the photodetector or fiber optic cable of the probe.

Figure 2:
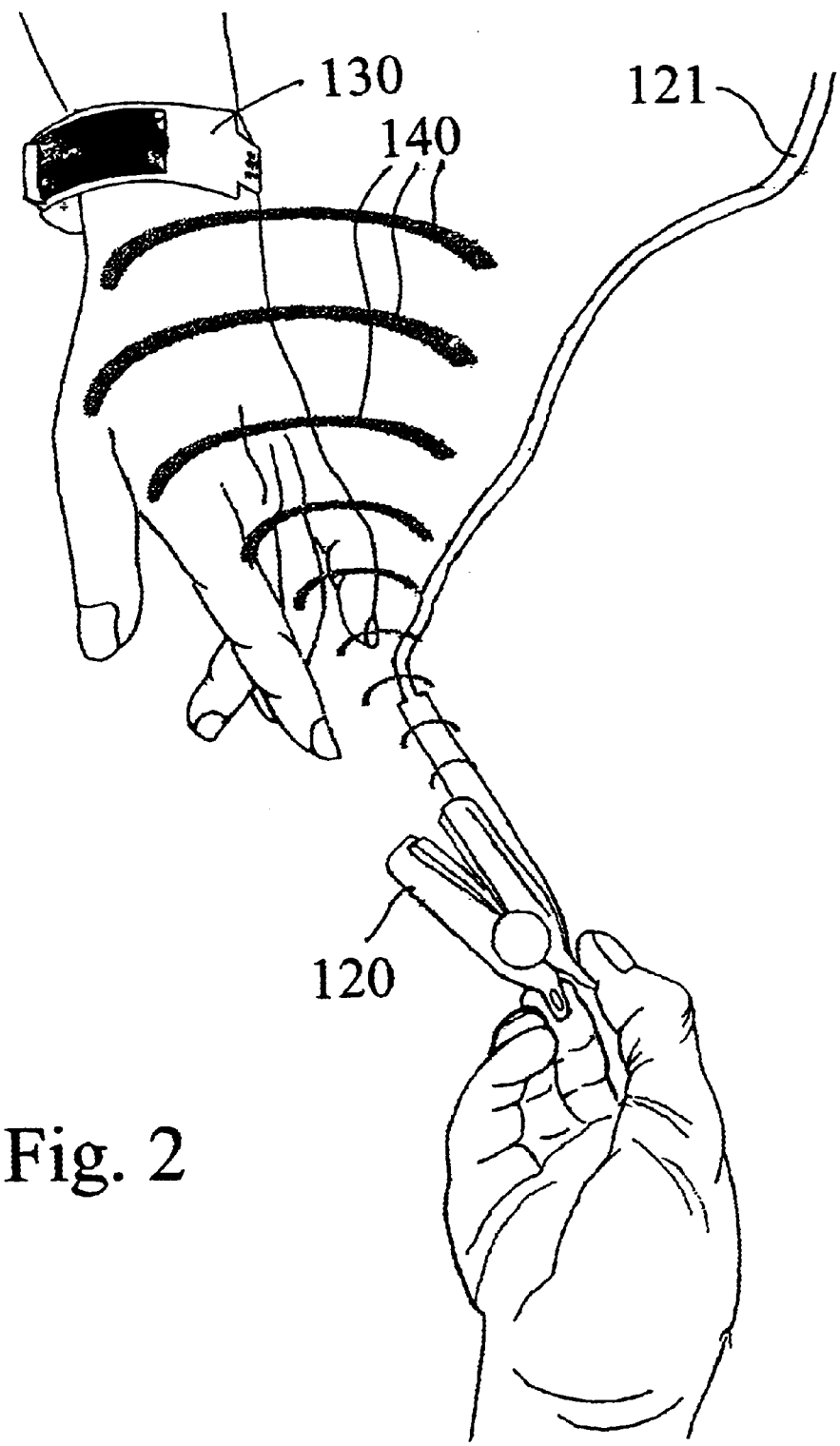
FIG. 2 is a perspective view of an alternate embodiment wherein the patient's wristband contains an RF chip which is read by an antenna carried by the pulse oximeter probe.

A somewhat different method of patient identification shown in FIG. 2 employs a radio frequency (RF) antenna in the body of the pulse oximeter probe 120 with the major portion of the electronics within the external monitor (not shown). This includes the radio frequency generator, the interpretative electronics, and software. The wristband 130, itself, rather than having a bar code, would then utilize a pre-programmed chip and an antenna which are embedded in the wristband. Signal strength from the antenna can be adjusted so that the range of the probe's signal generator is 8 inches or less, therefore avoiding spurious signals from any other patient but the patient of interest. As the pulse oximeter probe 120 is passed over the wrist to be placed on the fingertip for a pulse oximeter reading, a signal is generated shown by wave pattern 140 which, being in the vicinity of the embedded chip, picks up the identification signal from the wristband 130, and the patient is thereby automatically identified by the patient monitor.

Once the patient is identified, his or her name and identification number may be displayed on the monitor. The patient data including blood oxygen saturation is automatically placed into the monitor's memory alongside the patient's name and identification number. Downloading to a computer can be done after taking a succession of patient vital signs, each group of vital signs conveniently tagged with the patient's identification number and name.

The advantage of using a pulse oximeter probe for patient identification is that it is invariably passed over the patient's wrist as the probe is moved toward the patient's finger. Therefore in essentially one motion, the nurse accomplishes both a pulse oximeter reading and patient identification.

Bar code readers are well known in the art and are available off the shelf in a form that can be easily modified and adapted to the present invention. An example is the Model WDR R11/12 made by Worth Data of Santa Cruz, Calif. For use with a pulse oximeter probe, a fiber optic cable connection 21 to the probe 20 enables the light source and detector to reside inside the external monitor (not shown) to which the pulse oximeter probe is connected by a cable. FIG. 1 shows how light from the end of the pulse oximeter probe 20 can be directed at the patient's wristband and reflected back from the bar code area back to the fiber optic inside the probe. Alternately, LED's and a detector can be carried at the end of the pulse oximeter probe. The detected signal is then sent back to the monitor where it is processed to derive the patient's ID.

Another method of patient identification using a pulse oximeter probe is to use the probe in conjunction with a radio frequency patient ID system. In such a system, the major portion of the electronics is within the external monitor and the radio signal is carried by a co-axial cable 121 to an antenna within the pulse oximeter probe. The complete read-write system is contained within the external monitor. Such a system can utilize a reader chip such as a Phillip HTR C110 which is designed for easy integration into an RF Identification System. The antenna for the read-write system is carried under the top surface of the oximeter probe 120 and may be composed of a grid of fine wires printed on flexible circuit board material. The RF signal easily penetrates the ABS plastic of the probe. The target of the RF signal is a patient's ID wristband such as described in U.S. Pat. No. 5,973,598 assigned to Precision Dynamics. This patent describes a programmable encoder circuitry formed on a flexible substrate with signal generating circuitry and antenna. All circuitry is printed on the flexible substrate with conductive ink. A similar identification tag is described in U.S. Pat. No. 5,914,862 assigned to Kasten Close Applied Research of Canada. FIG. 2 shows this embodiment in which a co-axial cable conducts the RF signal to the antenna of the pulse oximeter probe, from which it is transmitted to the RF ID tag on the patient's wrist.

In summary, both embodiments of this invention allow a convenient method whereby a pulse oximeter probe can be used to identify a patient while employing the probe to simultaneously take blood oxygen saturation readings from the patient's finger. The patient ID can be displayed, stored within the monitor and later entered into the hospital's electronic record system.

The foregoing description of the invention has been presented for purposes of illustration and description and is not intended to be exhaustive or to limit the invention to the precise form disclosed. Modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

What is claimed is:

1. A system for determining and storing patient identification and blood oxygen saturation and other vital signs from a plurality of patients, comprising:
   a portable pulse oximeter having a probe adapted to be temporarily placed onto a patient's finger to determine said patient's blood oxygen saturation,
   a patient wristband having either a unique bar code or a unique RF reader chip identifying each patient,
   means carried by said portable pulse oximeter probe for reading said patient's wristband and obtaining said patient's identification simultaneously with determining said patient's blood oxygen saturation, and
   storage means in said portable pulse oximeter for storing the identification of each of said plurality of patients together with said blood oxygen saturation reading and other vital signs measured for each of said plurality of patients.

2. The system of claim 1 wherein said means for reading each wristband comprises light means on said portable pulse oximeter probe which can be directed onto said wristband to read said bar code.

3. The system of claim 1 wherein said means for reading each comprises a coaxial cable from said portable pulse oximeter with an antenna from said coaxial cable and means for causing an RF signal to be sent from said antenna to said chip and receiving the return signal.

4. The system of claim 1 further comprising data storage means onto which said patient identification for each of said plurality of patients and said vital signs, including blood oxygen saturation, may be periodically downloaded and stored.

5. An apparatus for determining and storing patient identification and blood oxygen saturation and storing other vital signs taken from a plurality of patients wherein each of said patients wears a wristband having either a unique bar code or a unique RF reader chip identifying each patient comprising:
   a portable pulse oximeter having a probe adapted to be temporarily placed onto a patient's finger to determine said patient's blood oxygen saturation,
   means carried by said portable pulse oximeter probe for reading said patient's wristband and obtaining said patient's identification simultaneously with determining said patient's blood oxygen saturation, and
   storage means in said portable pulse oximeter for storing the identification of each of said plurality of patients together with said blood oxygen saturation reading and other vital signs measured for each of said plurality of patients.

6. The apparatus of claim 5 wherein each of said plurality of patients wears a wristband having a unique bar code identifying said patient and wherein said means for reading each wristband comprises light means carried by said portable pulse oximeter probe which can be directed onto said wristband to read said bar code.

7. The apparatus of claim 5 wherein each of said plurality of patients wears a wristband having an RF reader chip uniquely identifying each patient and wherein said means for reading each wristband comprises a coaxial cable from said portable pulse oximeter with an antenna in said coaxial cable and means for causing an RF signal to be sent from said antenna to said chip to be received.

8. The apparatus of claim 5 further comprising means for periodically downloading said patient identification for each of said plurality of patients and said vital signs, including blood oxygen saturation to data storage means.

9. A method for determining and storing patient identification and blood oxygen saturation and storing other vital signs taken from a plurality of patients wherein each of said patients wears a wristband having either a unique bar code or a unique RF reader chip identifying each patient, comprising the steps:
   temporarily placing a portable pulse oximeter probe on a finger of each of said patients to determine blood oxygen saturation,
   using said portable pulse oximetry probe to read the wristband worn by each of said patients to determine the identification of each patient simultaneously with determining blood oxygen saturation for each patient,
   determining one or more other vital signs from each of said plurality of patients, and
   storing in said portable pulse oximeter each of said patients' identification and the patients' respective blood oxygen saturation and other vital sign or signs.

10. The method of claim 9 comprising the further step:
   periodically downloading said stored patient identifications and said blood oxygen saturation and other vital sign readings for each of said patients from said portable pulse oximeter into a storage medium functioning as a vital signs record.

* * * * *